(12) United States Patent
Kanno

(10) Patent No.: US 12,340,710 B2
(45) Date of Patent: Jun. 24, 2025

(54) INFORMATION PROCESSING DEVICE AND ASSISTANCE SYSTEM

(71) Applicant: RIVERFIELD INC., Tokyo (JP)

(72) Inventor: Takahiro Kanno, Tokyo (JP)

(73) Assignee: RIVERFIELD INC., Tokyo (JP)

(*) Notice: Subject to any disclaimer, the term of this patent is extended or adjusted under 35 U.S.C. 154(b) by 34 days.

(21) Appl. No.: 18/363,794

(22) Filed: Aug. 2, 2023

(65) Prior Publication Data

US 2023/0377473 A1 Nov. 23, 2023

Related U.S. Application Data

(63) Continuation of application No. PCT/JP2021/004163, filed on Feb. 4, 2021.

(51) Int. Cl.
  *G09B 5/02* (2006.01)
  *G06T 11/60* (2006.01)

(52) U.S. Cl.
  CPC ............ *G09B 5/02* (2013.01); *G06T 11/60* (2013.01); *G06T 2200/24* (2013.01)

(58) Field of Classification Search
  CPC .......... G09B 5/02; G06T 11/60; G06T 220/24
  See application file for complete search history.

(56) References Cited

U.S. PATENT DOCUMENTS

| | | | |
|---|---|---|---|
| 6,490,490 B1 * | 12/2002 | Uchikubo | A61B 1/04 700/246 |
| 6,652,452 B1 * | 11/2003 | Seifert | A61B 1/00096 600/140 |
| 6,659,940 B2 * | 12/2003 | Adler | A61B 6/504 600/129 |
| 6,728,599 B2 * | 4/2004 | Wang | A61B 34/70 600/595 |
| 6,834,207 B2 * | 12/2004 | Miyauchi | A61B 5/00 700/83 |
| 6,843,793 B2 * | 1/2005 | Brock | A61B 17/00 606/130 |
| 6,852,107 B2 * | 2/2005 | Wang | A61B 34/70 600/407 |
| 9,569,889 B2 * | 2/2017 | Chen | G06F 3/04847 |
| 10,319,128 B2 * | 6/2019 | Billi-Duran | G06F 3/011 |
| 11,102,425 B2 * | 8/2021 | Takanashi | G06F 3/0425 |
| 11,249,714 B2 * | 2/2022 | Spivack | A63F 13/69 |
| 11,617,559 B2 * | 4/2023 | Samec | A61B 5/024 345/633 |

(Continued)

FOREIGN PATENT DOCUMENTS

| | | |
|---|---|---|
| JP | 2000-271147 A | 10/2000 |
| WO | 2012/081194 A1 | 6/2012 |

*Primary Examiner* — Xuan M Thai
*Assistant Examiner* — Sadaruz Zaman
(74) *Attorney, Agent, or Firm* — Sughrue Mion, PLLC

(57) ABSTRACT

An information processing device in an instruction-side system of an assistance system comprising an operation-side system and the instruction-side system separated from the operation-side system, the information processing device comprising a processor configured to transmit drawing information based on an operation input to the operation-side system, generate annotation image data based on the drawing information, and receive image data from the operation-side system and combine the image data with the annotation image data.

17 Claims, 6 Drawing Sheets

(56) References Cited

U.S. PATENT DOCUMENTS

| | | | |
|---|---|---|---|
| 11,672,534 B2* | 6/2023 | Shelton, IV | G16H 40/20 |
| | | | 227/175.1 |
| 11,779,268 B2* | 10/2023 | Liu | A61B 5/6831 |
| | | | 705/3 |
| 11,883,022 B2* | 1/2024 | Shelton, IV | A61B 18/14 |
| 11,889,976 B2* | 2/2024 | Charles | A61B 17/16 |
| 11,896,195 B2* | 2/2024 | Thomas | A61B 1/00004 |
| 11,911,030 B2* | 2/2024 | Shelton, IV | A61B 17/07207 |
| 11,963,683 B2* | 4/2024 | Shelton, IV | A61B 5/0075 |
| 11,992,372 B2* | 5/2024 | Shelton, IV | G06F 3/017 |
| 12,016,566 B2* | 6/2024 | Shelton, IV | G16H 40/20 |
| 2005/0033117 A1* | 2/2005 | Ozaki | G16H 40/63 |
| | | | 600/117 |
| 2008/0294000 A1 | 11/2008 | Iwamoto | |
| 2012/0256950 A1* | 10/2012 | Masuda | G16H 40/63 |
| | | | 345/629 |
| 2019/0005841 A1* | 1/2019 | Loi | G09B 5/02 |

* cited by examiner

INFORMATION PROCESSING DEVICE AND ASSISTANCE SYSTEM

CROSS-REFERENCE TO RELATED APPLICATION

This application is a continuation of International Application No. PCT/JP2021/004163, filed Feb. 4, 2021, the entire contents of which is incorporated by reference herein in its entirety.

BACKGROUND

The present disclosure relates to an assistance system including an operation-side system and an instructor-side system.

An assistance system is configured such that an operator, such as a surgical operator, can perform an operation, such as performing a surgical operation on a patient, while receiving instructions from an instructor at a remote location. This assistance system is used when, for example, a less experienced operation doctor (the surgical operator) performs surgery while receiving instructions from an experienced instruction doctor (an instructor).

SUMMARY

It is an aspect to provide a surgery assistance system in which an instructor at a remote location can assist a surgical operator.

According to an aspect of one or more embodiments, there is provided an information processing device included in an instruction-side system of an assistance system comprising an operation-side system and the instruction-side system separated from the operation-side system, the information processing device comprising at least one processor configured to at least transmit drawing information based on an operation input to the operation-side system; generate annotation image data based on the drawing information; and receive image data from the operation-side system and combine the image data with the annotation image data.

According to another aspect of one or more embodiments, there is provided an information processing device included in an operation-side system of an assistance system comprising the operation-side system and an instruction-side system separated from the operation-side system, the information processing device comprising at least one processor configured to at least receive drawing information based on an operation input from the instruction-side system and generate annotation image data from the drawing information; generate combined image data by combining input image data and the annotation image data; and transmit the combined image data generated by the image combining unit to the instruction-side system.

According to yet another aspect of one or more embodiments, there is provided an assistance system comprising: an operation-side system comprising a first information processing device; and an instruction-side system that is separated from the operation-side system and comprises a second information processing device, wherein the first information processing device comprises at least one first processor configured to: generate first annotation image data based on drawing information received from the instruction-side system; generate first combined image data by combining input image data and the first annotation image data; and transmit the first combined image data to the instruction-side system, and the second information processing device comprises at least one second processor configured to: transmit the drawing information to the first information processing device; generate a second annotation image data based on the drawing information; and receive the first combined image data and generate second combined image data by combining the second annotation image data and the first combined image data.

BRIEF DESCRIPTION OF DRAWINGS

The above and/or the other aspects will become apparent and more readily appreciated from the following description of exemplary embodiments, taken in conjunction with the accompanying drawings, in which.

DETAILED DESCRIPTION

Figure 1:
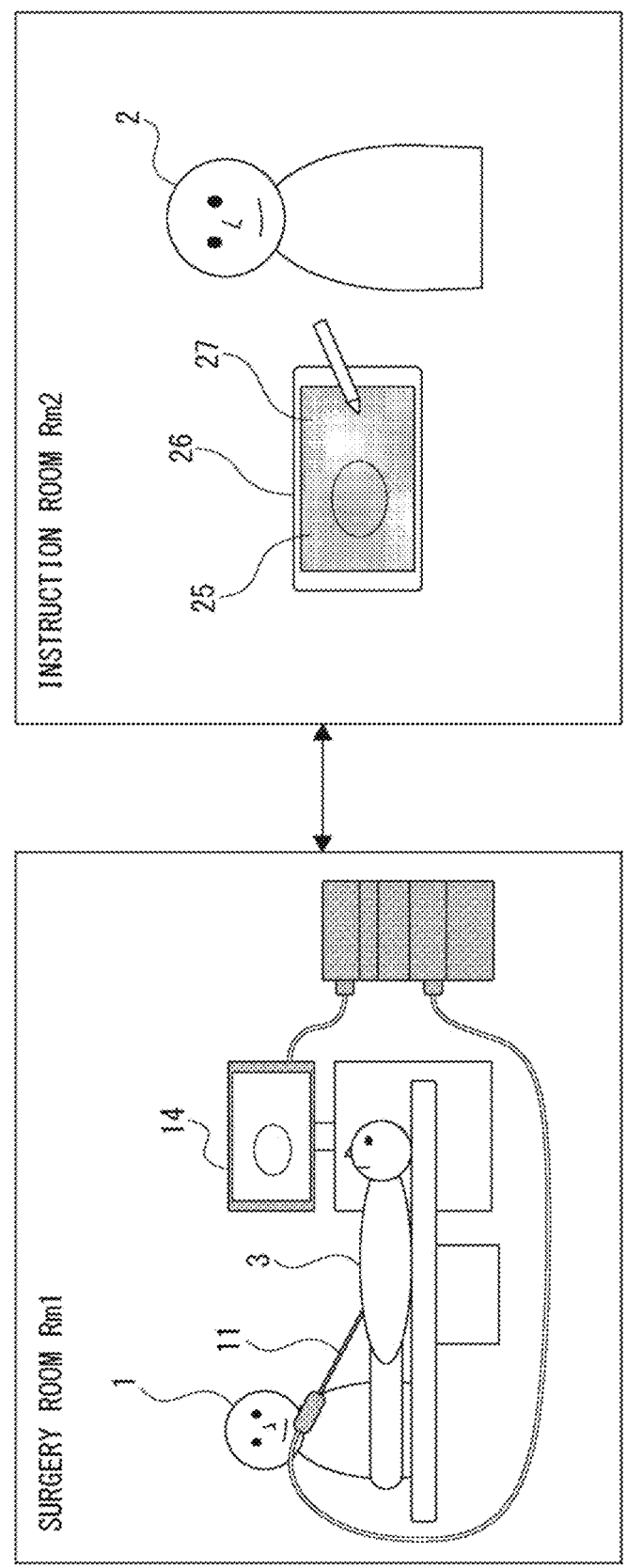
FIG. 1 is a drawing illustrating an outline of an assistance system according to some embodiments.

According to the related art, a monitor displaying a captured image (hereinafter also noted as an endoscope image) by an endoscope inserted into a patient may be located at a remote location, and an instruction doctor at the remote location may input instructions while observing the endoscope image displayed on the monitor. On the other hand, on a monitor on a surgery room side, a combined image where instruction contents input at the remote location are superimposed on the endoscope image may be displayed, and an operation doctor may perform surgery on the patient while receiving the instructions of the instruction doctor at the remote location.

The related art assistance system allows an instructor to observe captured images displayed on a monitor and to provide instructions. Thus, even a less experienced surgical operator can perform reliable surgical operation on a patient, and skills of the surgical operator himself/herself can also be improved.

However, when such an assistance system is employed in a field where safety of a surgical operation subject (a patient) of the above-described endoscopic surgery and the like is required, in order to allow a surgical operator during surgery to confirm a state of a patient in real time, it is advantageous that an endoscope image on which instruction contents of an instructor are reflected be displayed on a monitor on a surgical operator side at as low latency as possible.

In order for the instructor side also to input the instruction contents without a sense of incompatibility, it is advantageous that the endoscope image on which the input is reflected be displayed on the monitor of the instructor himself/herself at as low latency as possible.

It is thus an aspect to provide an assistance system in which an instructor at a remote location can perform appropriate assistance to a surgical operator.

According to some embodiments, an information processing device is included in a second system of an assistance system including a first system and the second system separated from the first system. The information processing device may include a data transmission unit that transmits drawing information that is based on an operation input and is necessary for generating annotation image data, to the first system; an image generation unit that generates the annotation image data from the drawing information; and an image combining unit that combines the annotation image data generated by the image generation unit and image data received from the first system.

The annotation image data may be image data that is superimposed on an endoscope image and may be image data generated based on the drawing information.

The drawing information may denote information such as a coordinate, a line type, a color, and a line width specified by the operation input.

According to some embodiments, in the first system in the above-described assistance system, the annotation image data may be generated from the drawing information, and combined image data may be generated by combining the generated annotation image data and captured image data, and in the information processing device included in the second system, the image combining unit may combine the combined image data received from the first system and the annotation image data generated by the image generation unit.

This configuration generates the annotation image data at each of the first system and the second system.

In some embodiments, in the first system, the annotation image data may be generated from the drawing information, and combined image data may be generated by combining a plurality of pieces of image data including the generated annotation image data, and the image combining unit of the information processing device included in above-described the second system may combine the combined image data received from the first system and the annotation image data generated by the image generation unit.

This configuration allows confirmation of whether or not the drawing information transmitted to the first system side is reflected on the combined image data received from the first system, on the second system side.

In some embodiments, the image generation unit may generate annotation image data that is distinguishable from the annotation image data included in the combined image data.

This configuration allows distinguishing a display based on the annotation image data included in the combined image data from a display based on the annotation image data generated by the image generation unit, and allows confirming whether or not the annotation image data on which the drawing information based on the input at the second system is reflected is generated on the first system side.

According to some embodiments, an information processing device may be included in a first system of an assistance system including the first system and a second system separated from the first system. The information processing device may include an image generation unit that receives drawing information based on an operation input from the second system and generates annotation image data from the received drawing information; an image combining unit that generates combined image data by combining image data that is input and the annotation image data generated by the image generation unit; and a data transmission unit that transmits the combined image data generated by the image combining unit, to the second system.

In some embodiments, when the combined image data is generated on the first system side, instead of the annotation image data, the drawing information having a communication volume less than the annotation image data may be received from the second system.

In some embodiments, a delay time from when a plurality of image data are input until when the combined image data may be output by the image combining unit is considered to be less than 30 milliseconds.

As a result, when the display based on the input image data is performed on the monitor on the first system side, the surgical operator visually recognizing the monitor does not feel any delay.

In some embodiments, the assistance system may include the information processing device included in the above-described first system and the information processing device included in the above-described second system. The assistance system may be achieved by each of the information processing devices described above communicating with one another.

In some embodiments, the instruction contents, which are based on the input of the instructor at a remote location, displayed on each of the monitors of the surgical operator side and the instructor side with significantly low latency allow the surgical operator and the instructor to share the instruction contents in real time.

The following describes various embodiments with reference to FIGS. 1 to 9. Each configuration described in the referenced drawings merely indicates one example for achieving the present disclosure. Accordingly, it is possible to make various modifications corresponding to design and the like as long as they are within the scope not departing from the technical idea of the present disclosure. In order to avoid duplication for the configuration that has been described once, identical reference numerals are given hereinafter, and re-description will be omitted, in some cases.

<1. Outline of Assistance System>

An assistance system 100 in which a surgical operator 1 in a surgery room Rm1 can perform surgery on a patient 3 while confirming instructions by an instructor 2 in an instruction room Rm2 separated from the surgery room Rm1 provided in some embodiments will be described. In the surgery assistance system, for example, the surgical operator 1 is an operation doctor for the patient 3, and the instructor 2 is an instruction doctor instructing the operation doctor.

Figure 2:
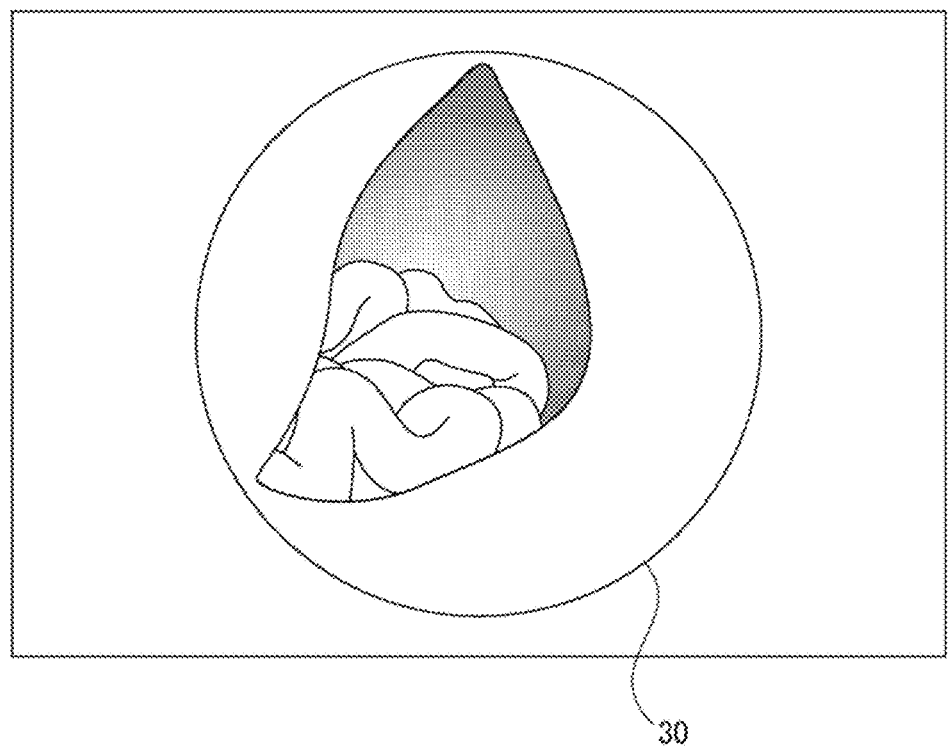
FIG. 2 is a drawing illustrating an endoscope image according to some embodiments.

For example, by inserting an endoscope 11 into a body cavity of the patient 3, an endoscope image 30 inside the body cavity illustrated in FIG. 2 is displayed on a monitor 14 in the surgery room Rm1. The surgical operator 1 can confirm the endoscope image 30 on the monitor 14.

The endoscope image 30 is also displayed on a monitor 25 of an instruction terminal 26 disposed in the instruction room Rm2. The instructor 2 can confirm the endoscope image 30 by the monitor 25 while staying in the instruction room Rm2.

The instruction terminal 26 is, in some embodiments, a tablet terminal having a touch panel 27, and the instructor 2 can input instruction contents on the endoscope image 30 by operating the touch panel 27 with his/her finger or a stylus pen.

Figure 3:
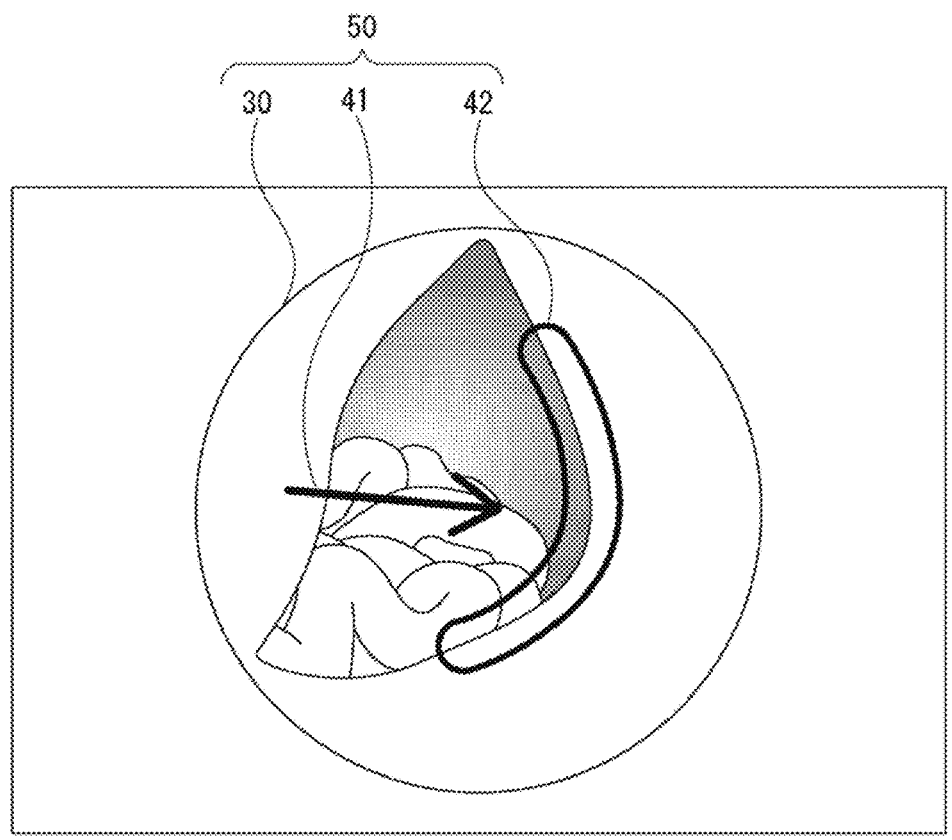
FIG. 3 is a drawing illustrating a combined image where an annotation image is superimposed on the endoscope image according to some embodiments.

A combined image 50 in which annotation images 41, 42 indicating the instruction contents of the instructor 2 as illustrated in FIG. 3 are superimposed on the endoscope image 30 is displayed on the monitor 14. The surgical operator 1 can perform a surgical operation on the patient 3 while referencing (confirming with) the instructions of the instructor 2 displayed on the monitor 14.

Instruction contents, which are based on the input of the instructor at a remote location, displayed on each of monitors of the surgical operator side and the instructor side with significantly low latency allow the surgical operator and the instructor to share the instruction contents in real time A monitor displaying a captured image (hereinafter also noted as an endoscope image) by an endoscope inserted into a patient is located at a remote location, and an instruction doctor at the remote location can input instructions while observing the endoscope image displayed on the monitor. At the same time, on a monitor on a surgery room side, a combined image where instruction contents input at the remote location are superimposed on the endoscope image is displayed, and an operation doctor can perform surgery on the patient while receiving the instructions from the instruction doctor at the remote location. The assistance system allows an instructor to observe captured images displayed on a monitor and to provide instructions. Thus, even a less experienced surgical operator can perform reliable surgical operation on a patient, and skills of the surgical operator himself/herself can also be improved.

<2. Configuration of Assistance System>

Figure 4:
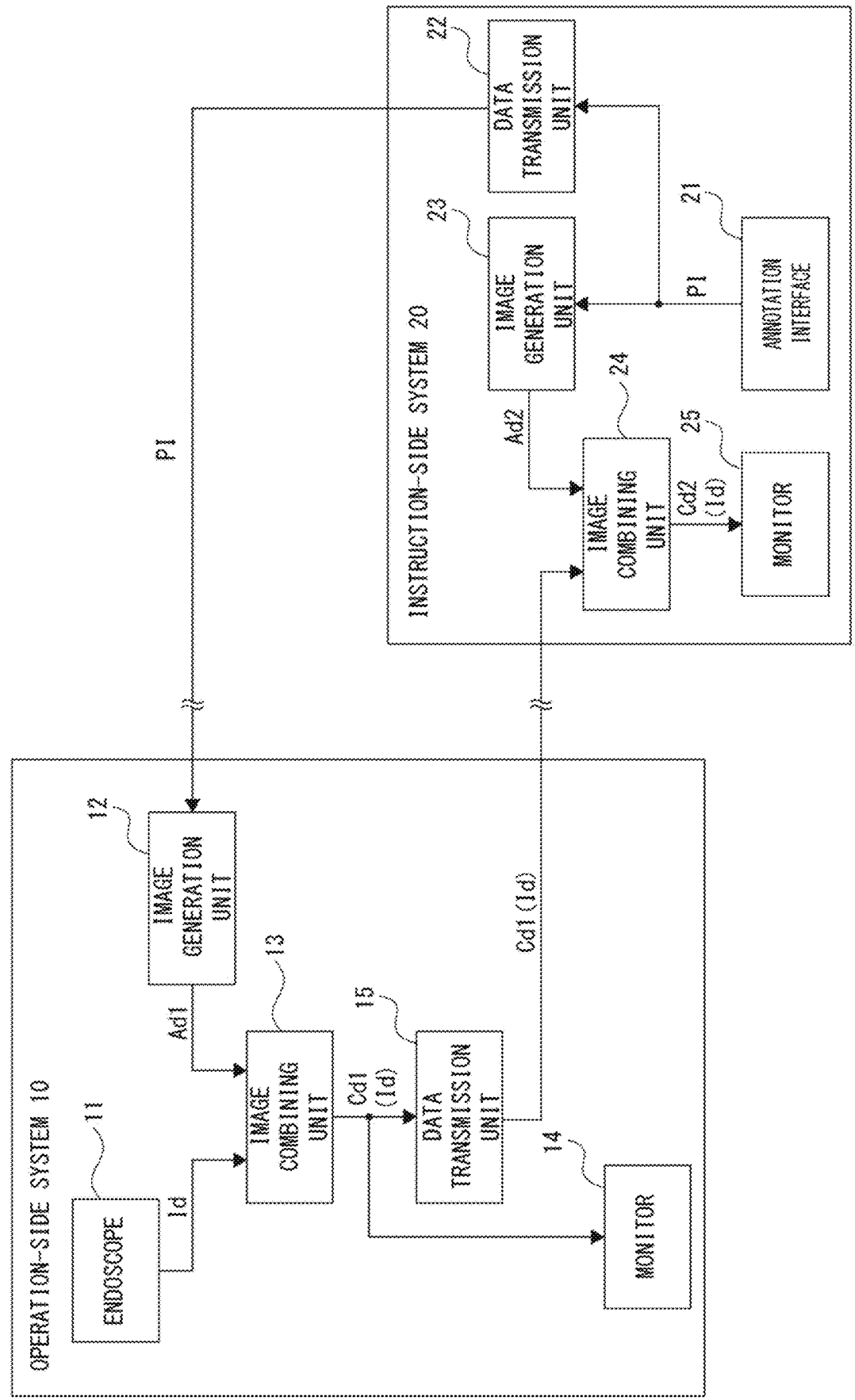
FIG. 4 is a drawing schematically illustrating one example of a configuration of the assistance system according to some embodiments.

The configuration of the assistance system 100 will be described. FIG. 4 is a block diagram illustrating the configuration of the assistance system 100 according to some embodiments.

As illustrated in FIG. 4, the assistance system 100, according to some embodiments, includes an operation-side system 10 constituted on the surgery room Rm1 side and an instruction-side system 20 constituted on the instruction room Rm2 side. The operation-side system 10 and the instruction-side system 20 are separated from one another and can communicate with one another through a wired or a wireless transmission line. In some embodiments, each of the operation-side system 10 and the instruction-side system 20 may include one or more memories and one or more processors. In some embodiments, each of the operation-side system 10 and the instruction-side system 20 may include hardware control logic.

The operation-side system 10 includes the endoscope 11, an image generation unit 12, an image combining unit 13, the monitor 14, and a data transmission unit 15. The one or more memories of the operation-side system 10 may store computer program code to implement the image generation unit 12, the image combining unit 13, and the data transmission unit 15, and the one or more processors of the operation-side system 10 may be configured to access the one or more memories to execute the computer program code to implement the image generation unit 12, the image combining unit 13, and the data transmission unit 15. In some embodiments, the hardware control logic of the operation-side system 10 may be configured to implement the image generation unit 12, the image combining unit 13, and the data transmission unit 15.

The endoscope 11 includes imaging devices, and captured image signals obtained by the imaging devices are each A/D converted and converted into endoscope image data Id, image data for displaying the endoscope image 30, representing a luminance value by predetermined gradation in a pixel unit.

The image generation unit 12 is constituted of, for example, an image processor or the like, and generates annotation image data Ad1 based on drawing information PI transmitted from the instruction-side system 20.

Here, the drawing information PI may include information such as a coordinate, a line type, a color, a line width that are specified by the operation input.

Figure 5:
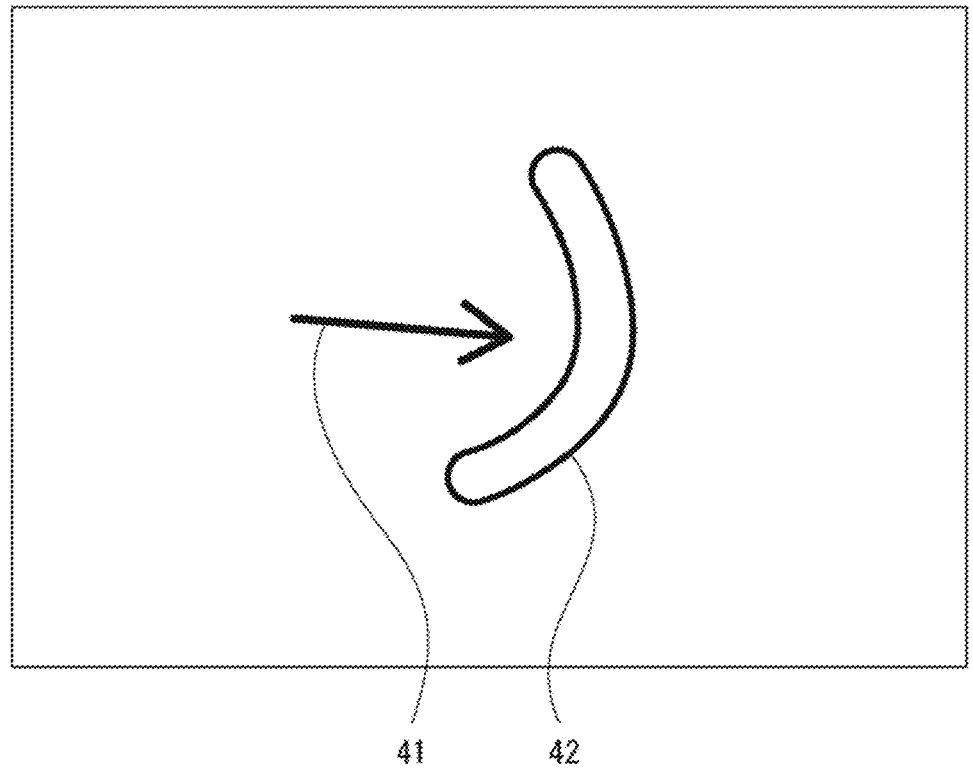
FIG. 5 is a drawing illustrating the annotation image according to some embodiments.

The annotation image data Ad1 is the image data, such as the annotation images 41, 42 illustrated in FIG. 5, generated based on the drawing information PI and to be superimposed on the endoscope image 30. This also applies to the annotation image data Ad2, which will be described later.

The image combining unit 13 may be, in some embodiments, a video mixer device constituted of hardware or a dedicated circuit implemented with a Field Programmable Gate Array (FPGA) and the like. The image combining unit 13 is configured to combine various types of input image data. In some embodiments, the image combining unit 13 combines the endoscope image data Id and the annotation image data Ad1 to generate operation-side combined image data Cd1.

The monitor 14 may be, for example, a liquid crystal display device or the like. The monitor 14 is configured to display an image on a display panel based on the supplied image data. In some embodiments, a display based on the supplied endoscope image data Id or operation-side combined image data Cd1 is performed on the monitor 14.

The data transmission unit 15 is configured, in some embodiments, to be able to communicate with the instruction-side system 20 and can transmit various types of data to the instruction-side system 20. In some embodiments, the data transmission unit 15 transmits the endoscope image data Id or the operation-side combined image data Cd1 obtained from the image combining unit 13.

The instruction-side system 20 includes an annotation interface 21, a data transmission unit 22, an image generation unit 23, an image combining unit 24, and the monitor 25. The respective components may be integrally constituted as, in some embodiments, the instruction terminal 26. The one or more memories of the instruction-side system 20 may store computer program code to implement the annotation interface 21, the data transmission unit 22, the image generation unit 23, and the image combining unit 24, and the one or more processors of the instruction-side system 20 may be configured to access the one or more memories to execute the computer program code to implement the annotation interface 21, the data transmission unit 22, the image generation unit 23, and the image combining unit 24. In some embodiments, the hardware control logic of the instruction-side system 20 may be configured to implement the annotation interface 21, the data transmission unit 22, the image generation unit 23, and the image combining unit 24.

The annotation interface 21 may include, in some embodiments, input devices, such as a touch panel, a touchpad, a computer mouse, and a keyboard, a processor, and the like generating the drawing information PI corresponding to the operation input to those input devices. In some embodiments, an input to the annotation interface 21 is performed by operating the touch panel 27 in FIG. 1 by the instructor 2 with his/her finger, a stylus pen, or the like.

The data transmission unit 22 is configured to be able to communicate with the operation-side system 10 and can transmit various types of data to the operation-side system 10. In some embodiments, the data transmission unit 22 transmits the drawing information PI obtained by the annotation interface 21.

The image generation unit 23 may, in some embodiments, consist of an image processor or the like, and generates the annotation image data Ad2 from the drawing information PI.

The image combining unit 24 includes, in some embodiments, a video mixer device as hardware or a software mixer constituted in the information processing device and combines various kinds of pieces of supplied image data. In some embodiments, by the image combining unit 24, the annotation image data Ad2 is combined with the endoscope image data Id or the operation-side combined image data Cd1, and thus the instruction-side combined image data Cd2 is generated.

The monitor 25 may be, in some embodiments, a liquid crystal display device or the like. The monitor 25 is configured to display an image on a display panel based on the supplied image data. In some embodiments, a display based on the instruction-side combined image data Cd2 is performed.

In some embodiments, the image generation units 12, 23, the image combining units 13, 24, and the data transmission units 15, 22 are constituted of hardware. However, the constitution of each functional unit is not limited thereto. In some embodiments, all or a part of each functional unit may be achieved by one or a plurality of hardware devices. In some embodiments, any of each functional unit may be constituted as a microcomputer including a Central Processing Unit (CPU), a Read Only Memory (ROM), a Random Access Memory (RAM), and the like. In some embodiments, for example, each function can be achieved by the CPU executing processes based on a program as software stored in the ROM or the like.

<3. Details of Assistance System>

The assistance system 100 according to some embodiments will be described with reference to FIG. 4.

In the operation-side system 10, the endoscope image data Id obtained by the endoscope 11 is supplied to the image combining unit 13.

When the annotation image data Ad1 is not supplied from the image generation unit 12, the image combining unit 13 supplies the endoscope image data Id to the monitor 14 and the data transmission unit 15.

The endoscope image data Id is supplied to the monitor 14 and the endoscope image 30 is displayed on the monitor 14 (see FIG. 2), allowing the surgical operator 1 to observe a state inside the body cavity of the patient 3 on the monitor 14 while performing the surgical operation.

The data transmission unit 15 transmits the endoscope image data Id supplied from the image combining unit 13 to the instruction-side system 20.

In the instruction-side system 20, the image combining unit 24 receives the endoscope image data Id from the operation-side system 10 (the data transmission unit 15). When the annotation image data Ad2 is not supplied from the image generation unit 23, the image combining unit 24 supplies the endoscope image data Id to the monitor 25.

By the endoscope image data Id being supplied, the endoscope image 30 is displayed on the monitor 25 (see FIG. 2), allowing the instructor 2 to share a viewpoint with the surgical operator 1 in the surgery room Rm1 while remaining in the instruction room Rm2 and to observe the state inside the body cavity of the patient 3 and an operation status of the surgical operation by the surgical operator 1.

While observing the endoscope image 30 displayed on the monitor 25, the instructor 2 is able to input a pictorial figure, a character, a symbol, and the like indicating the instruction contents for the surgical operator 1 on the endoscope image 30 via the input devices, such as the touch panel 27.

In the annotation interface 21, the drawing information PI corresponding to the operation input to the touch panel 27 is generated. The drawing information PI obtained by the annotation interface 21 is supplied to the image generation unit 23 and the data transmission unit 22.

The data transmission unit 22 transmits the drawing information PI obtained from the annotation interface 21 to the operation-side system 10. In transmission to the operation-side system 10, by transmitting the drawing information PI having a communication volume less than the annotation image data Ad2 generated by the image generation unit 23, a communication delay when data is transmitted from the instruction-side system 20 to the operation-side system 10 is reduced.

In the operation-side system 10, the image generation unit 12 receives the drawing information PI from the instruction-side system 20 (the data transmission unit 22). The image generation unit 12 generates the annotation image data Ad1 for causing the annotation images 41, 42 (see FIG. 5) to be displayed from the received drawing information PI.

The annotation image data Ad1 generated by the image generation unit 12 is supplied to the image combining unit 13.

The image combining unit 13 combines the endoscope image data Id supplied from the endoscope 11 and the annotation image data Ad1 supplied from the image generation unit 12 to generate the operation-side combined image data Cd1. The operation-side combined image data Cd1 is the image data for causing the combined image 50 (see FIG. 3) in which the annotation images 41, 42 (see FIG. 5) are superimposed on the endoscope image 30 (see FIG. 2) to be displayed.

In some embodiments, since the image combining unit 13 is constituted of the video mixer device by the hardware, a delay time from when the endoscope image data Id and the annotation image data Ad1 are input until when the operation-side combined image data Cd1 is output is significantly short.

In some embodiments, the image combining unit 13 can also constitute a processor having a high computation capability. By the processor executing a combining process specified by a program, it is possible to achieve a processing speed comparable to that of the video mixer device by the hardware. In some embodiments, for example, a processing speed may be such that the delay time from input until output is less than 30 milliseconds. In such a case, the image combining unit 13 may be achieved as a software mixer.

By quickly performing the combining process at the above-described processing speed, the operation-side combined image data Cd1 generated by the combining process is supplied to the monitor 14 without delay and displayed on the monitor 14 with less time lag.

This efficient combining process allows the surgical operator 1 in the surgery room Rm1 to perform the surgical operation on the patient 3 without experiencing a time lag while confirming the instructions of the instructor 2 in the instruction room Rm2 on the monitor 14.

In an example embodiment in which the image combining unit 13 is the video mixer device by the hardware or a software mixer device using a processor having a significantly high processing speed, and a delay time is less than 30 milliseconds as described above, the surgical operator 1 is likely to feel almost no time lag with respect to the image.

The data transmission unit 15 transmits the operation-side combined image data Cd1 supplied from image combining unit 13 to the instruction-side system 20.

In the instruction-side system 20, the image generation unit 23 generates the annotation image data Ad2 for causing the annotation images 41, 42 (see FIG. 5) to be displayed, based on the drawing information PI obtained from the annotation interface 21. The annotation image data Ad2 obtained by the image generation unit 23 is supplied to the image combining unit 24.

The image combining unit 24 combines the operation-side combined image data Cd1 received from the operation-side system 10 (the data transmission unit 15) and the annotation image data Ad2 supplied from the image generation unit 23 to generate the instruction-side combined image data Cd2. The generated instruction-side combined image data Cd2 is supplied to the monitor 25.

When having received the endoscope image data Id instead of the operation-side combined image data Cd1 from the operation-side system 10, the image combining unit 24 combines the endoscope image data Id and the annotation image data Ad2 to generate the instruction-side combined image data Cd2. The instruction-side combined image data Cd2 generated at this time is supplied to the monitor 25, similarly as described above.

In some embodiments, since the annotation image data Ad2 is combined when the instruction-side combined image data Cd2 is generated, the combined image 50 (see FIG. 3) in which the annotation images 41, 42 (see FIG. 5) are superimposed on the endoscope image 30 (see FIG. 2) is displayed on the monitor 25.

Thus, by generating the instruction-side combined image data Cd2 in the instruction-side system 20, the instruction-side combined image data Cd2 can be supplied to the monitor 25 without delay compared with the case where the instruction-side combined image data Cd2 is generated on the operation-side system 10 based on the transmitted drawing information PI. This configuration allows for performing an image display on the monitor 25 while reducing stress on the instructor 2 performing an operation input on the touch panel 27.

In some embodiments, by further combining the annotation image data Ad2 on the operation-side combined image data Cd1 combined with the annotation image data Ad1 to generate the instruction-side combined image data Cd2, the instructor 2 can confirm on the monitor 25 whether or not there is any displacement in the annotation images 41, 42 displayed based on each of the operation-side combined image data Cd1 and the annotation image data Ad2.

Figure 6:
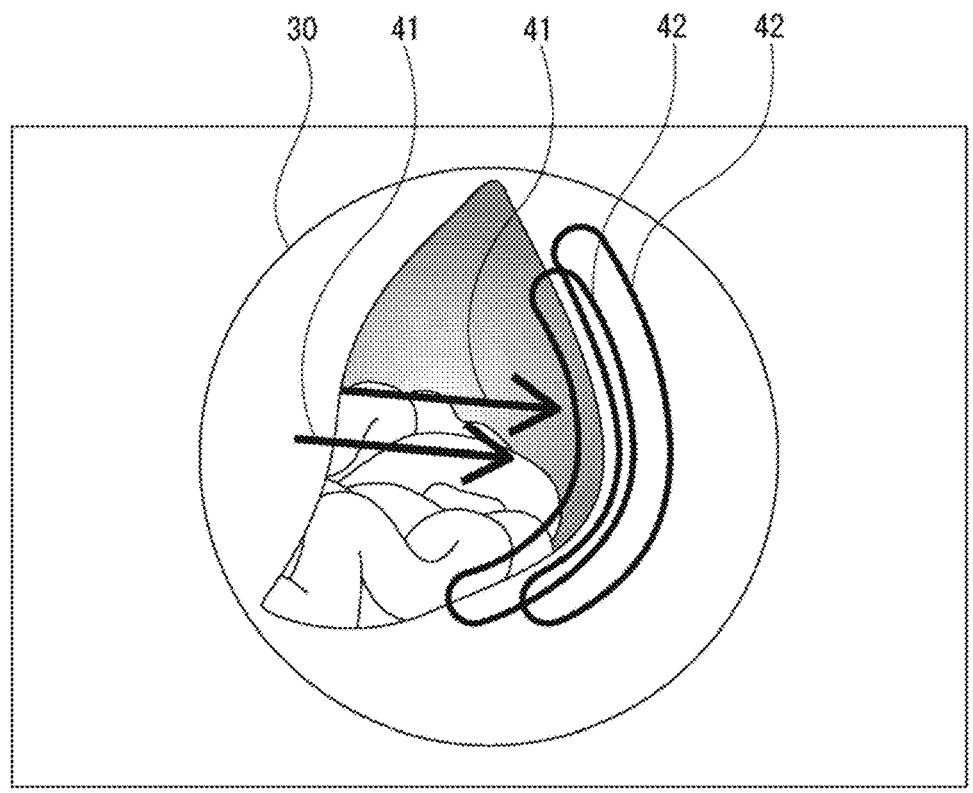
FIG. 6 is a drawing illustrating a combined image where annotation images are superimposed on the endoscope image according to some embodiments.

That is, if displacement occurs, the instructor 2 can confirm the displacements of the annotation images 41, 42 as illustrated in FIG. 6 on the monitor 25.

In some embodiments, in considering a point of confirmation of the display contents, the image generation unit 23 may generate the annotation image data Ad2 as image data having a display mode different from that of the annotation image data Ad1 generated by the image generation unit 12.

Figure 7:
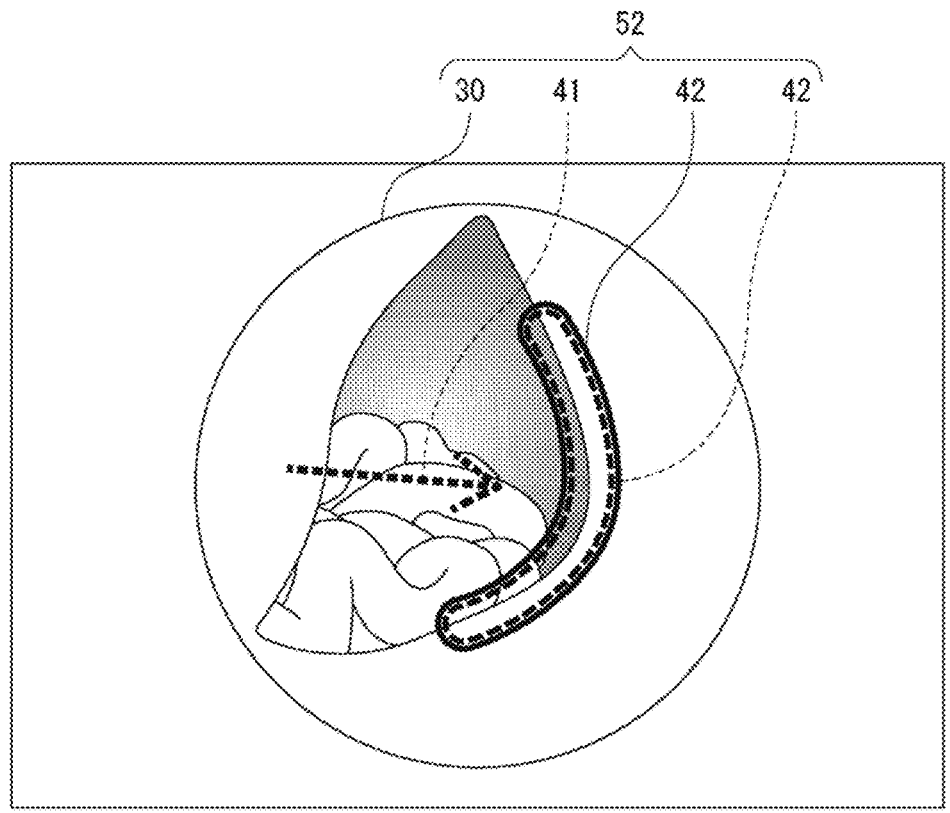
FIG. 7 is a drawing illustrating a combined image where annotation images are superimposed on the endoscope image according to some embodiments.

For example, in some embodiments as illustrated in FIG. 7, displaying the annotation images 41, 42 based on the annotation image data Ad2 with dashed lines allows displaying them to be on the monitor 25 in a state of being distinguished from the display (solid line) of the annotation image 42 based on the annotation image data Ad1 included in the operation-side combined image data Cd1.

In FIG. 7, the portion where the dashed line runs along the solid line is indicated as such for convenience of explanation and is actually a portion where the dashed line and the solid line overlap with one another.

As described above, causing both the annotation images 41, 42 based on the annotation image data Ad1 and the annotation images 41, 42 based on the annotation image data Ad2 to be displayed and allowing them to be confirmed has the following meaning.

In the drawing information PI transmitted from the instruction-side system 20, it is possible that a part of the drawing information PI is lost when received by the operation-side system 10 due to, for example, factors such as communication failure, and/or display coordinates of the annotation images 41, 42 and the like are displaced due to, for example, unadjusted settings between respective systems (10, 20) or unadjusted difference in resolution between the monitors 14 and 25, and the like.

For example, an image like FIG. 6 may be displayed on the monitor 25 due to displacement of the display coordinates.

Figure 8:
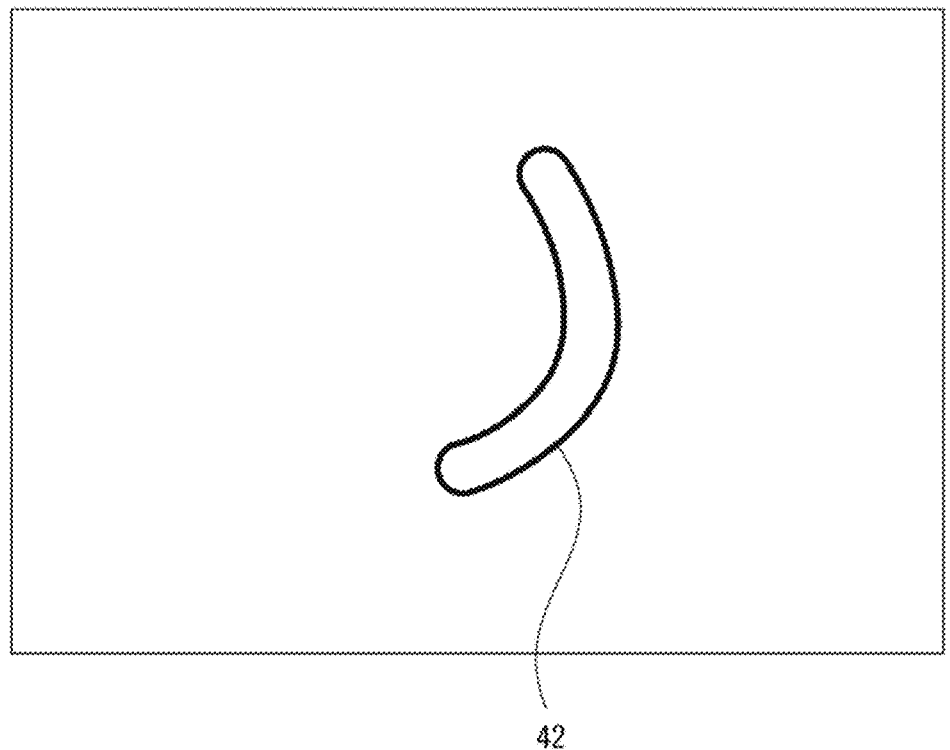
FIG. 8 is a drawing illustrating an annotation image according to some embodiments.

When a part of the information is lost, in the image generation unit 12 of the operation-side system 10, the annotation image data Ad1 for displaying the annotation images 41, 42 as illustrated in FIG. 5 are supposed to be generated based on the received drawing information PI. However, due to the loss of a part of the drawing information PI, the annotation image data Ad1 in which only the annotation image 42, as illustrated in FIG. 8, is displayed (hereinafter also noted as deficient annotation image data Ad1) may be generated.

Figure 9:
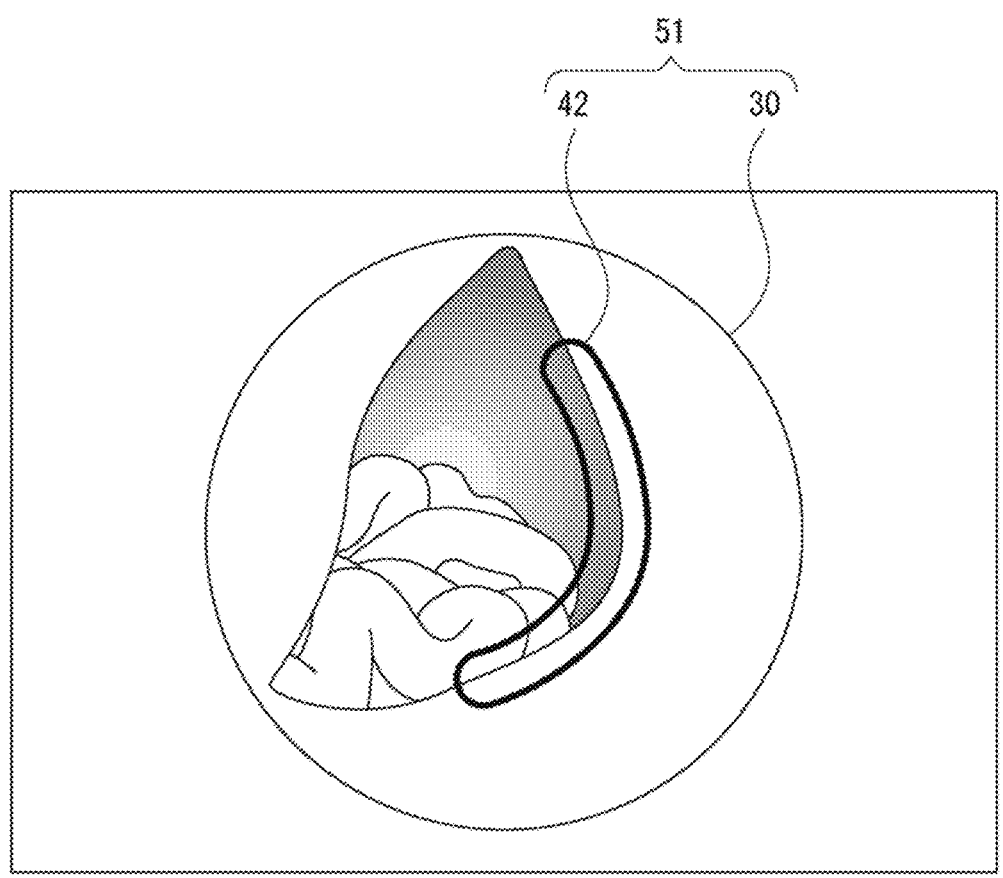
FIG. 9 is a drawing illustrating a combined image where an annotation image is superimposed on the endoscope image according to some embodiments.

In the image combining unit 13, the deficient annotation image data Ad1 generated by the image generation unit 12 and the endoscope image data Id are combined, and the combined image data Cd1 for displaying a combined image 51 in which only the annotation image 42 is superimposed on the endoscope image 30 is generated, as illustrated in FIG. 9.

Thus, based on the supplied operation-side combined image data Cd1, the combined image 51 lacking the annotation image 41 is displayed on the monitor 14. In such a state, the inputs of the instructor 2 are not accurately reflected on the monitor 14, and the surgical operator 1 performs the surgical operation in a state where the surgical operator 1 cannot grasp all of the instructions of the instructor 2.

In the instruction-side system 20, since the operation-side combined image data Cd1 received from the operation-side system 10 and the annotation image data Ad2 for displaying the annotation images 41, 42 generated by the image generation unit 23 are combined, the instruction-side combined image data Cd2 for displaying the combined image 50 (see FIG. 5) is generated regardless of whether or not the annotation image data Ad1 of the operation-side combined image data Cd1 is lost.

Since this displays the combined image 50 based on the instruction-side combined image data Cd2 on the monitor 25, the instructor 2 cannot confirm that the annotation image 41 is lost in the display of the monitor 14 on the surgical operator 1 side. In order for the instructor 2 to confirm the display condition of the monitor 14 on the surgical operator 1 side, it is advantageous to cause the images based on the annotation image data Ad1, Ad2 to be displayed in a different mode.

Thus, the image generation unit 23 generates the annotation image data Ad2 for causing the annotation images 41, 42 to be displayed by, for example, dashed lines, based on the drawing information PI.

The image combining unit 24 combines the annotation image data Ad2 supplied from the image generation unit 23 and the operation-side combined image data Cd1 received from the operation-side system 10 to generate the combined image data Cd2.

By the generated instruction-side combined image data Cd2 being supplied to the monitor 25, a combined image 52 as illustrated in FIG. 7 is displayed on the monitor 25.

This configuration allows the instructor 2 to confirm that the portion of the annotation image 41 displayed with only the dashed line is not displayed on the monitor 14 in the operation-side system 10.

That is, on the monitor 25, the instructor 2 can easily compare his/her own instruction contents with the contents on the monitor 14 viewed by the surgical operator 1.

As described above, by observing the image based on the instruction-side combined image data Cd2, the instructor 2 can see both the images based on the annotation image data Ad1, Ad2 and can confirm whether or not his/her own instructions are correctly transmitted to the surgical operator 1. By being able to recognize that the instructions by the image were not correctly transmitted, the instructor 2 can take necessary countermeasures.

In some embodiments, as an example of a display mode for distinguishing the annotation image data Ad1 from the annotation image data Ad2 in the instruction-side combined image data Cd2, the dashed line and the solid line are used to perform distinction. However, the display mode is not limited thereto as long as each of the annotation image data Ad1 and the annotation image data Ad2 is distinguishable. In some embodiments, the distinction can be performed by differentiating the line type such as the line width, the color, the luminance, or the like. The distinction can be performed by highlighting any one of them.

Among the annotation image data Ad2 generated by the image generation unit 23, it is also conceivable to distinguish and display a portion that does not match the annotation image data Ad1.

<4. Modifications>

According to some embodiments, the assistance system 100 includes a first system (the operation-side system 10) and a second system (the instruction-side system 20) separated from the operation-side system 10.

The information processing device included in the instruction-side system 20 may include the data transmission unit 22, the image generation unit 23, and the image combining unit 24 (see FIG. 4).

The data transmission unit 22 transmits the drawing information PI based on the operation input, which is necessary for generating the annotation image data Ad1, to the operation-side system 10. The image generation unit 23 generates the annotation image data Ad2 from the drawing information PI. Further, the image combining unit 24 combines the annotation image data Ad2 generated by the image generation unit 23 and the operation-side combined image data Cd1 (or the endoscope image data Id) received from the operation-side system 10.

By generating the annotation image data Ad2 and combining the generated annotation image data Ad2 and the operation-side combined image data Cd1 (or the endoscope image data Id) to generate the instruction-side combined image data Cd2 in the instruction-side system 20, the instruction-side combined image data Cd2 can be obtained more quickly than receiving one generated by the operation-side system 10.

Accordingly, the instructor 2 can confirm the pictorial figure and the like input by himself/herself on the monitor 25 without being affected by communication delay or the like. Consequently, since the instructor 2 can comfortably and accurately perform the input, appropriate instructions for the surgical operator 1 can be performed.

According to some embodiments, the image generation unit 23 of the instruction-side system 20 generates the annotation image data Ad2 that is distinguishable from the annotation image data Ad1 included in the operation-side combined image data Cd1.

This configuration allows distinguishing the display based on the annotation image data Ad1 from the display based on the annotation image data Ad2 and confirming whether or not the annotation image data Ad1 reflecting the drawing information PI based on the input in the instruction-side system 20 is generated in the operation-side system 10 (see FIG. 7).

Accordingly, the instructor 2, who is looking at the monitor 25, can easily confirm whether or not his/her own instruction contents are appropriately displayed on the monitor 14 at which the surgical operator 1 is looking.

According to some embodiments, the information processing device included in the operation-side system 10 includes the image generation unit 12, the image combining unit 13, and the data transmission unit 15 (see FIG. 4).

The image generation unit 12 receives the drawing information PI based on the operation input from the instruction-side system 20 and generates the annotation image data Ad1 from the received drawing information PI. The image combining unit 13 combines the input image data (the endoscope image data Id) and the annotation image data Ad1 generated by the image generation unit 12 to generate the operation-side combined image data Cd1. Further, the data transmission unit 15 transmits the operation-side combined image data Cd1 (or the endoscope image data Id) generated by the image combining unit 13 to the instruction-side system 20.

Here, when the operation-side combined image data Cd1 is generated in the operation-side system 10, instead of the annotation image data Ad2, the drawing information PI having the communication volume less than the annotation image data Ad2 is received from the instruction-side system 20. This configuration allows reducing the communication delay when the data is transmitted to the operation-side system 10 from the instruction-side system 20 and generating the annotation image data Ad1 based on the drawing information PI without delay in the operation-side system 10.

The instructions by the instructor 2 can be displayed on the monitor 14 without delay, and the surgical operator 1 can immediately confirm the instructions from the instructor 2. Thus, the surgical operator 1 can perform a safer surgical operation on the patient 3.

In some embodiments, while the example in which the image data input to the image combining unit 13 is the endoscope image data Id has been described, the input image data is not limited to the captured image data like the endoscope image data Id supplied from the endoscope 11. In some embodiments, image data recorded in a memory and obtained by reading from the memory, image data received from an external computer device or the like, and the like can be considered in various manners as input image data.

In some embodiments, it is advantageous that the delay time from when the endoscope image data Id and the annotation image data Ad1 are input until the operation-side combined image data Cd1 is output by the image combining unit 13 is less than 30 milliseconds.

Since this configuration allows the surgical operator 1 to visually recognize the combined image 50 and the like on the monitor 14 with low latency, the accurate and safety surgical operation can be performed on the patient 3 with the instructions of the instructor 2 confirmed.

In some embodiments, as one example of the assistance system 100, the surgery assistance system in which the surgical operator 1 can perform the surgical operation on the patient 3 while receiving the instructions of the instructor 2 at a remote location has been described. However, the assistance system 100 can be widely applied to a situation in which the instructor 2 at a remote location gives the instructions to the surgical operator 1 while visually recognizing the captured image on the operation-side.

For example, the assistance system 100 can be applied to various uses, such as athletes and head coaches in sports instruction, instructors and students in learning assistance, such as education and vocational training, and presenters and listeners in remote conferences.

In some embodiments, while the example in which the endoscope 11 captures the image as illustrated in FIG. 1 has been described, it is only necessary that an image capturing device is one that can capture an image of the surgical operation on the surgical operator 1 side, and it is not limited to the endoscope 11.

In some embodiments, as one example of the instruction terminal 26 in FIG. 1, the tablet terminal having the touch panel has been described, but the instruction terminal 26 is not limited thereto. In some embodiments, the instruction terminal 26 can be achieved by various devices, for example, a computer mouse for an operation input, a Personal Computer (PC) having a keyboard and the like, a Virtual Reality (VR) having a head-mounted display and a remote controller for an operation input, a master console for a surgical robot, and the like.

The embodiments described in the present disclosure are merely examples, and the present disclosure is not limited to the above-described embodiments. All combinations of the configurations described in the embodiment are not necessarily required for solving the problem. Furthermore, the effects described in the present disclosure are merely examples and not limited, and other effects may be achieved, or a part of the effects described in the present disclosure may be achieved.

What is claimed is:

1. An information processing device included in an instruction-side system of an assistance system including an operation-side system and the instruction-side system that is a separate system from the operation-side system, the information processing device comprising at least one processor configured to:
   transmit, to the operation-side system, drawing information generated based on an operation input performed in the instruction-side system;
   generate annotation image data based on the drawing information; and
   receive, from the operation-side system, image data from the operation-side system and combine the image data received from the operation-side system with the annotation image data.

2. The information processing device according to claim 1, wherein
   the at least one processor is configured to receive first combined image data from the operation-side system and generate combined image data by combining the first combined image data with the annotation image data to generate combined image data, the first combined image data being a combination of a plurality of pieces of image data including first annotation image data generated in the operation-side system based on the drawing information.

3. The information processing device according to claim 2, wherein
   the at least one processor is configured to generate the annotation image data such that the annotation image data is distinguishable from the first annotation image data included in the first combined image data.

4. The information processing device according to claim 2, wherein the at least one processor is further configured to transmit the combined image data to a display configured to display the combined image data.

5. The information processing device according to claim 1, wherein the at least one processor is configured to receive the drawing information from a user interface, and
   wherein the drawing information corresponds to the operation input in the user interface.

6. An information processing device included in an operation-side system of an assistance system including the operation-side system and an instruction-side system that is a separate system from the operation-side system, the information processing device comprising at least one processor configured to at least:
   receive, from the instruction-side system, drawing information generated based on an operation input performed in the instruction-side system and generate annotation image data from the drawing information;
   generate combined image data by combining input image data and the annotation image data; and
   transmit the combined image data to the instruction-side system.

7. The information processing device according to claim 6, wherein
   a delay time from a time at which the input image data and the annotation image data are input until a time at which the combined image data is output is less than 30 milliseconds.

8. The information processing device according to claim 6, wherein the input image data is captured image data.

9. The information processing device according to claim 6, wherein the at least one processor is further configured to generate the combined image data by superimposing the annotation image data on the input image data.

10. The information processing device according to claim 6, wherein the at least one processor is further configured to transmit the input image data to the instruction-side system.

11. An assistance system comprising:
   an operation-side system including a first information processing device; and
   an instruction-side system that is a separate system from the operation-side system and includes a second information processing device, wherein
   the first information processing device includes at least one first processor configured to:
     generate first annotation image data based on drawing information received from the instruction-side system;
     generate first combined image data by combining input image data and the first annotation image data; and
     transmit the first combined image data to the instruction-side system, and
   the second information processing device includes at least one second processor configured to:
     transmit the drawing information to the first information processing device;

generate a second annotation image data based on the drawing information; and receive the first combined image data and generate second combined image data by combining the second annotation image data and the first combined image data.

12. The assistance system according to claim 11, wherein:

the operation-side system includes a first display configured to display the first combined image data, and the instruction-side system includes a second display configured to display the second combined image data.

13. The assistance system according to claim 12, wherein the drawing information is received from a user interface, and wherein the drawing information corresponds to an operation input in the user interface.

14. The assistance system according to claim 13, wherein the second display includes the user interface.

15. The assistance system according to claim 11, wherein the input image data is captured image data.

16. The assistance system according to claim 11, wherein the second annotation image data is distinguishable from the first annotation image data.

17. The assistance system according to claim 11, wherein the first combined image data is generated by superimposing the first annotation image data on the input image data.

* * * * *